(12) United States Patent
Woo

(10) Patent No.: US 10,589,056 B2
(45) Date of Patent: Mar. 17, 2020

(54) SLEEP INDUCING DEVICE AND SLEEP MANAGEMENT SYSTEM INCLUDING SAME

(71) Applicant: Frasen Inc., Seoul (KR)

(72) Inventor: Hyo Jun Woo, Daejeon (KR)

(73) Assignee: FRASEN INC., Seoul (KR)

( * ) Notice: Subject to any disclaimer, the term of this patent is extended or adjusted under 35 U.S.C. 154(b) by 340 days.

(21) Appl. No.: 15/526,681

(22) PCT Filed: Jul. 14, 2015

(86) PCT No.: PCT/KR2015/007282
§ 371 (c)(1),
(2) Date: May 12, 2017

(87) PCT Pub. No.: WO2016/140408
PCT Pub. Date: Sep. 9, 2016

(65) Prior Publication Data
US 2017/0312476 A1   Nov. 2, 2017

(30) Foreign Application Priority Data

Mar. 5, 2015 (KR) .................. 10-2015-0030703
Apr. 30, 2015 (KR) .................. 10-2015-0062025

(51) Int. Cl.
*A61M 21/02* (2006.01)
*A61M 21/00* (2006.01)

(52) U.S. Cl.
CPC ..... *A61M 21/02* (2013.01); *A61M 2021/0027* (2013.01); *A61M 2021/0044* (2013.01);
(Continued)

(58) Field of Classification Search
CPC .. A61M 2021/0027; A61M 2021/0044; A61M 21/02; A61M 2205/0216;
(Continued)

(56) References Cited

U.S. PATENT DOCUMENTS

2009/0105524 A1* 4/2009 Bressler ............ A61M 21/00
  600/27
2014/0343353 A1* 11/2014 Imran ................ G09B 5/04
  600/28

FOREIGN PATENT DOCUMENTS

KR  1020110064706 A   6/2011
KR  1020120092249 A   8/2012
(Continued)

OTHER PUBLICATIONS

International Search Report in International Application No. PCT/KR2015/007282, filed Jul. 14, 2015.

*Primary Examiner* — Christine H Matthews
(74) *Attorney, Agent, or Firm* — Saliwanchik, Lloyd & Eisenschenk

(57) ABSTRACT

A sleep inducing device and a sleep management system including the same are provided. The sleep inducing device comprises: a housing unit that includes a frame of which the shape can be changed; a sensor unit that is disposed on one surface of the housing unit and includes a brain-wave measurement sensor that measures a user's brain wave; an output unit that includes a first output unit and a second output unit, wherein the first output unit is located on one side of the housing unit to output a sound or light with a first frequency, and the second output unit is located on an opposite side of the housing unit to output a sound or light with a second frequency that is different from the first frequency; and a control unit that calculates the user's sleep pattern on the basis of the brain wave signal measured by the sensor unit and changes the output signal of the output unit such that the sleep pattern approaches a predetermined value.

8 Claims, 10 Drawing Sheets

(52) U.S. Cl.
CPC ............... *A61M 2205/0216* (2013.01); *A61M 2205/332* (2013.01); *A61M 2205/3306* (2013.01); *A61M 2205/3368* (2013.01); *A61M 2205/3375* (2013.01); *A61M 2205/3553* (2013.01); *A61M 2205/3561* (2013.01); *A61M 2205/3569* (2013.01); *A61M 2205/3592* (2013.01); *A61M 2205/502* (2013.01); *A61M 2205/505* (2013.01); *A61M 2205/52* (2013.01); *A61M 2230/005* (2013.01); *A61M 2230/10* (2013.01); *A61M 2230/18* (2013.01); *A61M 2230/50* (2013.01); *A61M 2230/63* (2013.01)

(58) Field of Classification Search
CPC ...... A61M 2205/3368; A61M 2230/18; A61M 2230/50
See application file for complete search history.

(56) References Cited

FOREIGN PATENT DOCUMENTS

| | | |
|---|---|---|
| KR | 1020120108491 A | 10/2012 |
| KR | 1020130005802 A | 1/2013 |
| KR | 1020140039452 A | 4/2014 |

\* cited by examiner

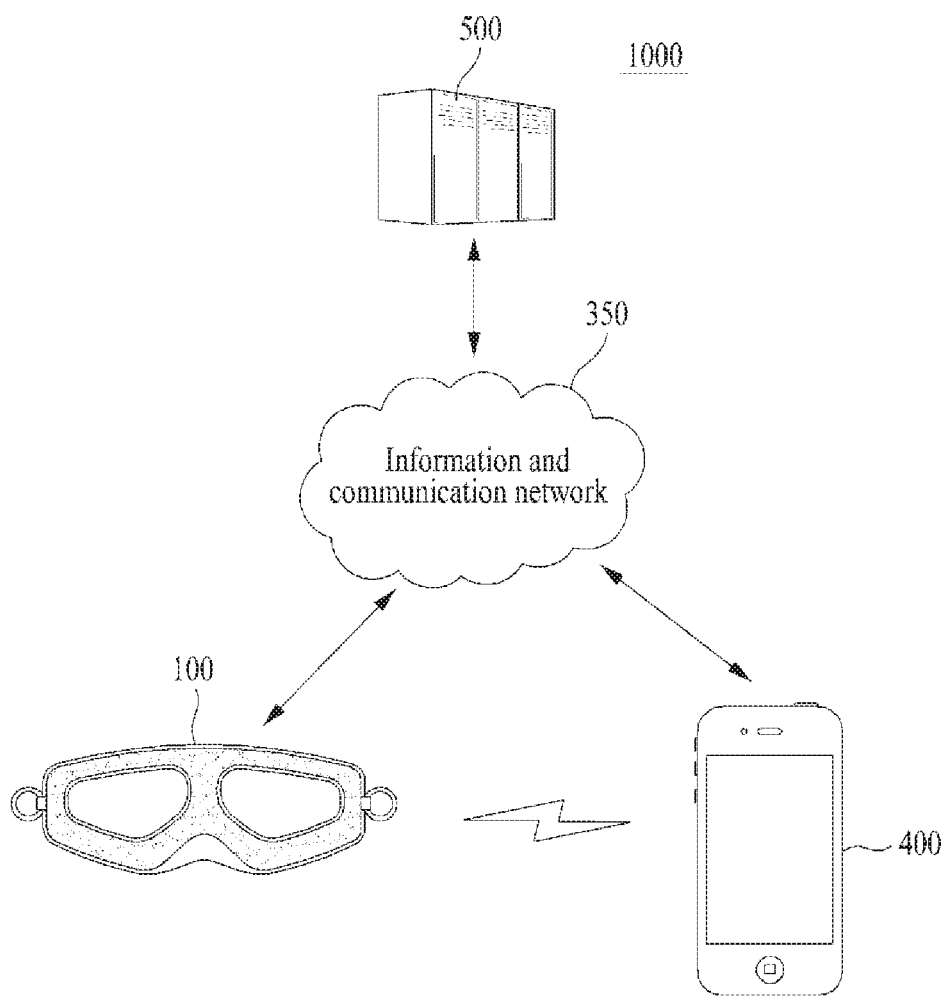

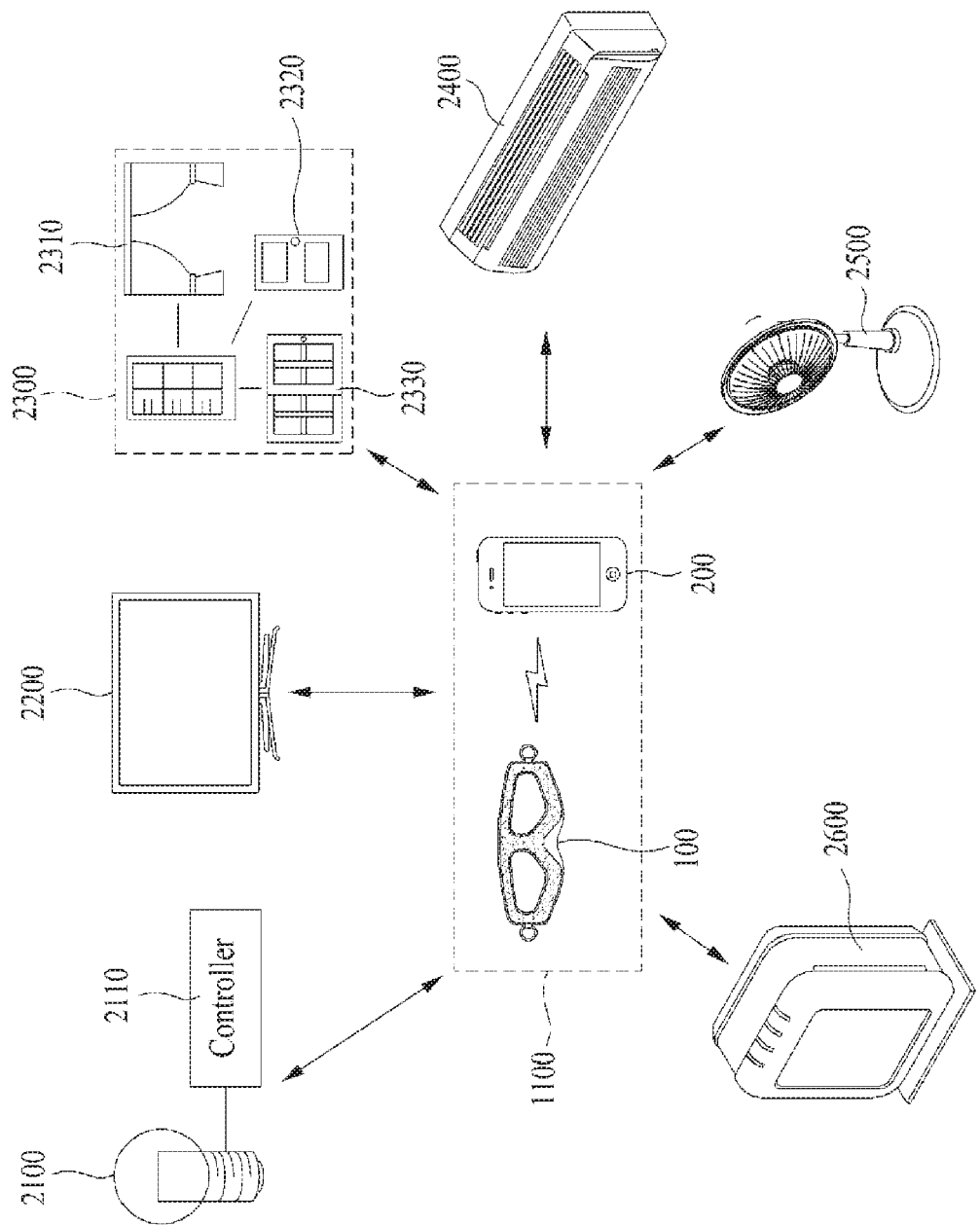

SLEEP INDUCING DEVICE AND SLEEP MANAGEMENT SYSTEM INCLUDING SAME

CROSS-REFERENCE TO RELATED APPLICATIONS

This application is the U.S. national stage application of International Patent Application No. PCT/KR2015/007282, filed Jul. 14, 2015; which claims priority to Korean Application Nos. 10-2015-0030703, filed Mar. 5, 2015; and 10-2015-0062025, filed Apr. 30, 2015, the disclosures of each of which are incorporated herein by reference in their entirety.

TECHNICAL FIELD

The present invention relates to a sleep inducing device and a sleep management system including the same. More particularly, the present invention relates to a sleep inducting device, capable of measuring a sleep state of a user and of inducing desirable sleeping, and a sleep management system including the same.

BACKGROUND ART

The sleep of a human being is significantly closely related to a brain wave. Brain waves are classified into alpha waves (7-14 Hz), beta waves (14-30 Hz), delta waves (0.5-4 Hz), and theta waves (4-8 Hz) depending on activity states of a brain. When alertness level is excessively high like an exercised state or a nervous state, the theta waves may mainly appear. In a sleepy state or a sleep state, the delta waves may mainly appear. In the state that the alertness level is excessively neither high nor low, the alpha waves or the theta waves may appear.

During sleeping, sleep types are mainly divided into Rapid Eye Movement (REM) sleep and non-REM sleep according to the types of brain waves. The non-REM sleep is generally sub-divided into four stages When a person is in a wakes-up state, the beta waves are mainly observed. Thereafter, if the person closes eyes and feels comfortable, the alpha waves starts increasing and the person falls into non-REM sleep. As the stage of the non-REM sleep passes, if the person more deeply falls asleep, the brain becomes calm to emit the delta waves. In this case, among sleep patterns, if a specific stage excessively less appears or frequently appears, mental or physical problems may be caused.

DETAILED DESCRIPTION OF THE INVENTION

Technical Problem

An object of the present invention relates to a sleep inducing device capable of measuring a sleep state based on a brain wave and of adjusting a sleep state of a user by using sound or light such that a substantially ideal sleep pattern is obtained based on the measured sleep state.

Another object of the present invention is to provide a sleep manage system capable of measuring a sleep state based on a brain wave, of adjusting a sleep state of a user by using sound or light such that a substantially ideal sleep pattern is obtained based on the measured sleep state, and of providing recommended life pattern for the user.

The objects which will be achieved in the present invention are not limited to the above, but other objects, which are not mentioned, will be apparently understood to those skilled in the art.

Technical Solution

In order to accomplish the objects, according to an aspect of the present invention, a sleep inducing device includes a housing unit including a frame allowing shape transformation, a sensor unit provided on one surface of the housing unit and including a brain-wave measurement sensor to measure a brain wave signal of a user, an output unit including a first output unit positioned at one side of the housing unit and to output sound or light of a first frequency, and a second output unit positioned at an opposite side of the housing unit and to output sound or light of a second frequency different from the first frequency, and a control unit to calculate a sleep pattern of the user based on the brain wave measured by the sensor unit and to change an output signal of the output unit such that the sleep pattern approaches a specific value.

According to some embodiments, the housing unit may include a cover part including a frame which is formed in an eye patch shape and allows the shape transformation in match with a head of the user, and an elastic part making contact with one surface of the cover part and including a material having elasticity.

According to some embodiments, in the housing part, an angle between a central portion and a side end portion may be adjusted from a first angle to a second angle by external force.

According to some embodiments, the sensor unit may further include a temperature sensor provided on the one surface of the housing unit and positioned on the same plane as a plane of the brain-wave measurement sensor, and an illuminance sensor or a humidity sensor provided on an opposite surface of the housing part.

According to some embodiments, a memory unit to store data, which is measured by the sensor unit, in real time; and a communication unit to wirelessly transmit the stored data to an external device may be further provided.

According to some embodiments, the data may include information on a brain wave or a body temperature of a user, or illuminance or humidity of an outside.

According to some embodiments, the control unit may adjust a sleep state of the user by adjusting an output frequency of the output unit such that a ratio between a REM sleep state and a non-REM sleep of the user is in a specific range.

According to some embodiments, the control unit may measure a response speed of a sleep state of the user based on a change in an output frequency and adjust a change rate of the output frequency based on the measured result.

According to some embodiments, the output unit may include a speaker unit including a first speaker to output the first frequency and a second speaker to output the second frequency making a difference from the first frequency by a first wavelength, and a second light source part including a first light source to adjust an intensity of light based on a change of the first frequency and a second light source to adjust an intensity of the light based on a change of the second frequency.

In order to accomplish the above object, according to an aspect of the present invention, a sleeping management system includes a sleep inducing device including a sensor unit to measure bio-information of a user and environment information on illuminance, temperature, or humidity, an output unit to simultaneously provide output signals of mutually different frequencies to a user through sound or light, a control unit to adjust an output signal of the output unit based on the bio-information and the environment information measured by the sensor unit, and a communication unit to wirelessly transmit the bio-information and the environment information, and a mobile device including an interface unit to receive the bio-information and the environment information, a computing unit to calculate sleep pattern information and recommended life pattern information of the user based on the bio-information and the environment information, which are received, and a display unit to the sleep pattern and the recommended sleep pattern.

According to some embodiments, the mobile device may receive the life pattern information, which includes an age, a gender, an average sleep time, an alcohol intake, or a caffeine intake of the user, and may transmit the life pattern formation to the sleep inducing device. The control unit of the sleep inducing device may change the output signal based on the bio-information, the environment information, and the life pattern information.

According to some embodiments, the control unit calculates an optimal sleep cycle including a ratio between a REM sleep state and a non-REM sleep state of the user, time of entering into the REM sleep state, or time of holding the REM sleep state, based on the bio-information, the environment information and the life pattern information, and adjusts an output frequency of the output unit to adjust an output signal such that the sleep state of the user approaches the optimal sleep cycle.

According to some embodiments, the control unit measures a change speed of the bio-information based on a change of the output signal of the output unit and adjusts a change rate of the output signal based on the measured result.

According to some embodiments, the sensor unit may include at least one of an EEG (electroencephalogram sensor, a PPG (photoplethysmogram) sensor, an EDA (electrodermal activity) sensor, an ECG (electrocardiogram) sensor, and an EMG (electromyogram) sensor.

According to some embodiments, the sleep state information may include change information of a sleep stage as a function of time, and the recommended life pattern information includes information on sleep time, wake-up time, a nutrient intake, recommended temperature, or recommended illuminance.

According to some embodiments, the mobile device may receive a sleep adaptation of the user, which is calculated based on a change rate of the life information resulting from a change of the output signal, from the sleep inducing device, may receive travel time difference information, which includes a departure location and a destination location, from the user, and may calculate recommended sleep information including recommended sleep time and recommended wake-up time based on the sleep adaptation and the travel time difference information and displays the recommended sleep information on a display.

The sleep inducing device or the mobile device may calculate the sleep state of the user based on the bio-information of the user and may output a wireless signal including a control signal to adjust the illuminance, temperature or humidity of the outside, based on the sleep state.

Other details of the present invention are included in the detailed description and drawings.

Advantageous Effects of the Invention

According to the present invention, the sleep inducing device and the sleep management system including the same may increase the quality of the sleep of the user. According to the present invention, the sleep state and the surrounding environment information of the user may be detected using various sensors, and change is applied to the output signal of sound or light based on the feedback using the detected information, thereby inducing the sleep state most suitable for the user. In addition, the shape of the sleep inducing device is changed to be suited to the facial shape of the user, thereby preventing the sleep of the user from being interrupted by external light.

In addition, there may be suggested a method of enabling the user to take quality sleep by providing the recommended life pattern information including sleep time, wake-up time, a nutrient intake, and recommended interior temperature, recommended interior which are illuminance most suitable for the user.

Further, recommended sleep information may be provided to help the user solve problems related to time difference adaptation, which may be caused in travelling.

The effects produced in the present invention are not limited to the above-mentioned effects, and other effects, which are not mentioned, will be apparently understood from the following description by those skilled in the art unless otherwise defined.

DESCRIPTION OF THE DRAWINGS

FIG. 9 is a view illustrating a sleep management system including a sleep inducing device, according to some embodiments of the present invention.

FIG. 10 is a view illustrating the operation of a sleep management system including a sleep inducing device, according to some embodiments of the present invention.

BEST MODE

Figure 1:
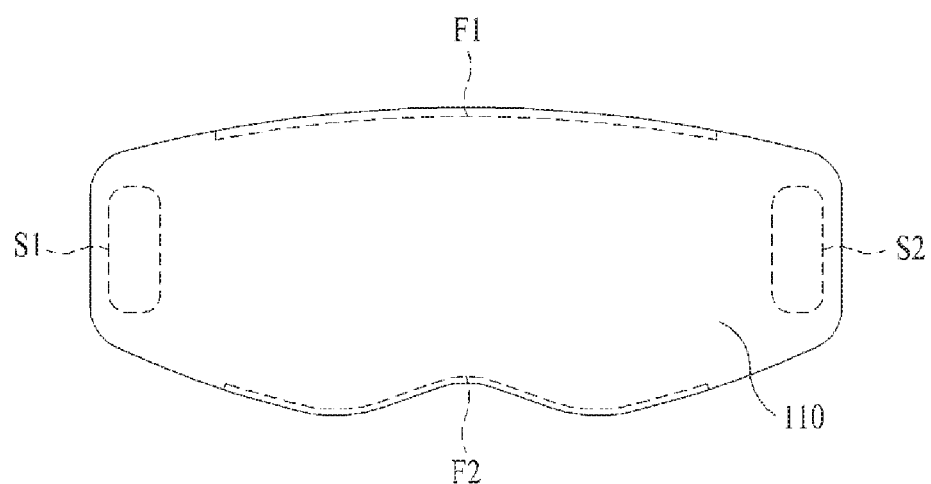
FIG. 1 is a front view illustrating a sleep inducing device, according to an embodiment of the present invention.

Advantage points and features of the prevent invention and a method of accomplishing thereof will become apparent from the following description with reference to the following figures, wherein embodiments will be described in detail with reference to the accompanying drawings. The present invention, however, may be embodied in various different forms, and should not be construed as being limited only to the illustrated embodiments. Rather, these embodiments are provided as examples so that this disclosure will be thorough and complete, and will fully convey the concept of the present invention to those skilled in the art. The present invention may be defined by scope of the claims. Meanwhile, the terminology used herein to describe embodiments of the invention is not intended to limit the scope of the present invention. Like reference numerals refer to like elements throughout the whole specification.

Spatially relative terms, such as "below", "beneath", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, when a device illustrated in accompanying drawings is reversed, a device provided 'below' or 'beneath' another device may be placed 'above' another device. Accordingly, the term "below" may include both concepts of "below" and "above. A device may be oriented in a different direction. Accordingly, terminology having relatively spatial concepts may be variously interpreted depending on orientations.

It will be understood that, although the terms "first", "second", etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, or section discussed below could be termed a second element, component, or section without departing from the teachings of the inventive concept.

The terminology used in the present invention is provided for the illustrative purpose, but the present invention is not limited thereto. As used herein, the singular terms "a," "an" and "the" are intended to include the plural forms as well, unless the context clearly indicates otherwise. Furthermore, it will be further understood that the terms "comprises", "comprising," "includes" and/or "including", when used herein, specify the presence of stated components, steps, operations, and/or devices, but do not preclude the presence or addition of one or more other components, steps, operations and/or devices.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. Suffixes such as "module" and "unit" may be used to refer to elements or components. Use of such a suffix herein is merely intended to facilitate description of the specification, and the suffix itself is not intended to give any special meaning or function Hereinafter, a sleep inducing device and a sleep management system including the same according to the present invention will be described in more detail with reference to accompanying drawings.

Figure 2:
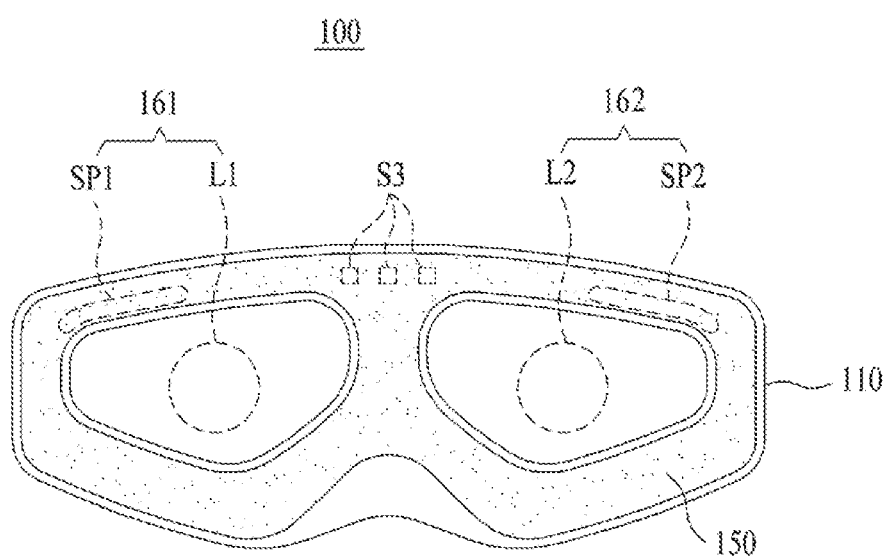
FIG. 2 is a rear view illustrating a sleep inducing device, according to an embodiment of the present invention.
Figure 3:
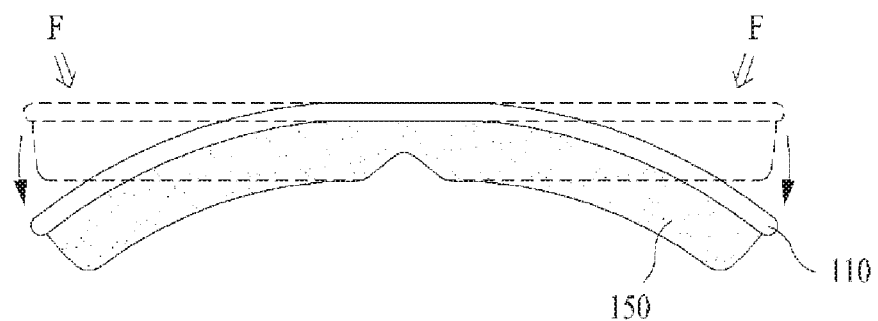
FIG. 3 is a side view illustrating shape transformation of a sleep inducing device, according to an embodiment of the present invention.

FIG. 1 is a front view illustrating a sleep inducing device, according to an embodiment of the present invention. FIG. 2 is a rear view illustrating the sleep inducing device, according to an embodiment of the present invention. FIG. 3 is a side view illustrating shape transformation of the sleep inducing device, according to an embodiment of the present invention.

Referring to FIGS. 1 to 3, according to an embodiment of the present invention, a sleep inducing device 100 may include housing parts 110 and 150, sensor units S1 to S3, and output units 161 and 162.

The housing parts 110 and 150 may include a cover part 110 and an elastic part 150. The cover part 110 may correspond to an outer surface of the housing parts 110 and 150, and the elastic part 150 may correspond to an inner surface of the housing parts 110 and 150.

The cover part 110 may be formed in the form to cover the eyes of a user, example, the cover part 110 may have the form of an eye patch. However, the present invention is not limited thereto.

The elastic part 150 may be formed to make contact with one surface of the cover part 110 and may include an elastic material. For example, the elastic part 150 may include a material, such as sponge, rubber, silicone, or the like, having an elastic property and providing a cushion feel. However, the present invention is not limited thereto. In addition, the elastic part 150 may directly make contact with a facial surface of a user. The elastic part 150 may be recessed at portions thereof overlapping eyes of the user and may have the form of putting on the nose of the user.

In detail, referring to FIG. 3, the cover part 110 may include a material allowing shape transformation. In the cover part 110, an angle between a central portion and a side end portion may be adjusted from a first angle (for example, the angle between the central portion and the side end portion is 0 degree; that is, the central portion and the side end portion are positioned on the same plane) to a second angle (for example, the angle between the central portion and the side end portion is in the range of 0 degree to 90 degrees) by external force F.

Referring to FIGS. 1 and 3, the cover part 110 may include frame parts F1 and F2 allowing shape transformation. The frame parts F1 and F2 may include a first frame F1 and a second frame F2. The first frame F1 may be positioned at an upper end of the cover part 110 and the second frame F2 may be positioned at a lower end of the cover part 110. In this case, the cover part 110 may be formed of an elastic material bendable at a specific angle. The first frame F1 and the second frame F2 may fix the shape or the angle of the cover part 110. However, the present invention is not limited thereto. For example, the entire portion of the cover part 110 may be subject to shape transformation by the external force F, or the cover part 110 may be formed of a material to fix the shape of the cover part 110 after the external force F is applied. The frame parts F1 and F2 may include materials having stiffness.

Accordingly, the shapes of the housing parts 110 and 150 may be changed to be matched with the shape of the facial surface of the user. Since users have various face lineaments, light may be infiltrated into the space between the housing parts 110 and 150 and the facial surface. In the sleep inducing device 100 of the present invention, the shapes of the housing parts 110 and 150 are changeable to be suited to the shape of the facial surface of the user. Accordingly, the sleeping of the user may be prevented from being interrupted by external light.

A first sensor unit S1 and a second sensor unit S2 may be provided on the cover part 110 (that is, the outer surface of the housing parts 110 and 150). As illustrated in FIG. 1, the first sensor unit S1 and the second sensor unit S2 may be provided at both sides of the cover part 110, but the present invention is not limited thereto. The first and second sensor units S1 and S2 may include illuminance sensors, which measure the illuminance of a user's surrounding environment, a temperature sensor, which measures the temperature of the outside, a humidity sensor, which measures the humidity of the outside, a microphone, which measures a sound emitted during the sleeping of the user or the external sound, and a motion sensor used for acquiring the motion of the user. The first and second sensor units S1 and S2 may be an acceleration sensor, a gyro sensor, a magnetic sensor, a gravity sensor, and the like.

Referring to FIG. 2, a third sensor unit S3 and output units 161 and 162 may be provided in the elastic part 150 (that is, on inner surfaces of the housing parts 110 and 150).

The third sensor unit S3 may be positioned at an upper central portion of the elastic part 150. However, this is provided for the illustrative purpose and the present invention is not limited thereto. The third sensor unit S3 may include at least one of an electroencephalogram (EEG) sensor, which is to acquire a brain wave of a user (hereinafter referred to as an EEG sensor), a PPG sensor, which is to acquire oxygen saturation of the user, an EDA sensor, which is to acquire user's tension, a temperature sensor, which is to acquire the temperature of a user's body, an ECG sensor, which acquires the heart rate of the user, an EMG sensor, which is to acquire the movement of user's body muscles, and an EOG sensor which is to acquire the movement of an user's eyeball.

The output units 161 and 162 may include a first output unit 161 and a second output unit 162. The first output unit 161 may be positioned at one side of the elastic part 150 to output sound or light of a first frequency. The second output unit 162 may be positioned at an opposite side of the elastic part 150 to output sound or light of a second frequency different from the first frequency.

The output units 161 and 162 may include speaker units SP1 and SP2, which output sound, and light source parts L1 and L2 which emit light. However, the present invention is not limited thereto. For example, the output units 161 and 162 may stimulate at least one of the user's five senses through at least one of vibration, sound, light, taste, and smell. For example, the output units 161 and 162 may further include a perfume output unit, which sprays a substance containing fragrance, and a vibration output unit which generates vibration.

The speaker units SP1 and SP2 may include a first speaker SP1, which outputs a first frequency, and a second speaker SP2 which outputs a second frequency different from the first frequency by a first wavelength. For example, the first speaker SP1 may be positioned at left upper ends of the housing parts 110 and 150 and the second speaker SP2 may be positioned at right upper ends of the housing parts 110 and 150. However, the present invention is not limited thereto.

In detail, the first speaker SP1 and the second speaker SP2 simultaneously output sound waves having mutually different frequencies to induce a brain wave or a sleep state of the user. In general, an audible frequency, which may be detected by a human being, is in the range of 20 Hz to 20 kHz. The brain waves (for example, alpha waves (7-14 Hz), beta waves (14-30 Hz), delta waves (0.5-4 Hz), and theta waves (4-8 Hz)) of the human being are equal to or less than the audible frequency (<20 Hz). Accordingly, a proper frequency may not be transmitted to a brain in a typical manner (to the contrary, in the case of light, when stimulation corresponding to a brain wave in a sleep stage, is arbitrarily set, the brain wave synchronization may be made.)

Accordingly, the sleep inducing device 100 may induce a brain wave by using a binaural beat. This is accomplished by using a principle of transmitting a frequency, which corresponds to the frequency difference between sound waves propagated to both ears of a human being, to a brain when the sound waves having mutually different frequencies are propagated to both ears of the human being. The details thereof will be described below with reference to FIG. 9.

In addition, the speaker units SP1 and PS2 may be used to remove external noise. For example, when noise is caused in a room, the speaker units SP1 and SP2 provide sound waves having frequencies different from those of the noise, thereby canceling the noise.

The light source parts L1 and L2 may include a first light source L1 to adjust the intensity of light based on the change of the first frequency and a second light source L2 to adjust the intensity of light based on the change of the second frequency. For example, the first light source L1 may be positioned at a left recess part of the housing parts 110 and 150, and the second light source L2 may be positioned at a right recess part of the housing parts 110 and 150. In other words, the first light source L1 irradiates light to a left eye of the user, and the second light source L2 irradiates light to a right eye of the user. However, the present invention is not limited thereto. The first light source L1 and the second light source L2 may include at least one LED or a light emitting member.

In other words, the first light source L1 may output light having the first frequency, and the second light source L2 may output light having the second frequency. The light source parts and L2 may employ the principle of the above described binaural beat. In this case, the change in the light intensities, color, and light illuminance of the light source parts L1 and L2 may be made based on the first frequency and the second frequency. For example, sound volumes may correspond to the light intensities of the light source parts L1 and L2, and the change in a sound type may correspond to the change in the color of light from the light source parts L1 and L2. In addition, the light source parts L1 and L2 may be used to output color that most greatly affects the sleep induction of the user. However, the present invention is not limited thereto.

Figure 4:
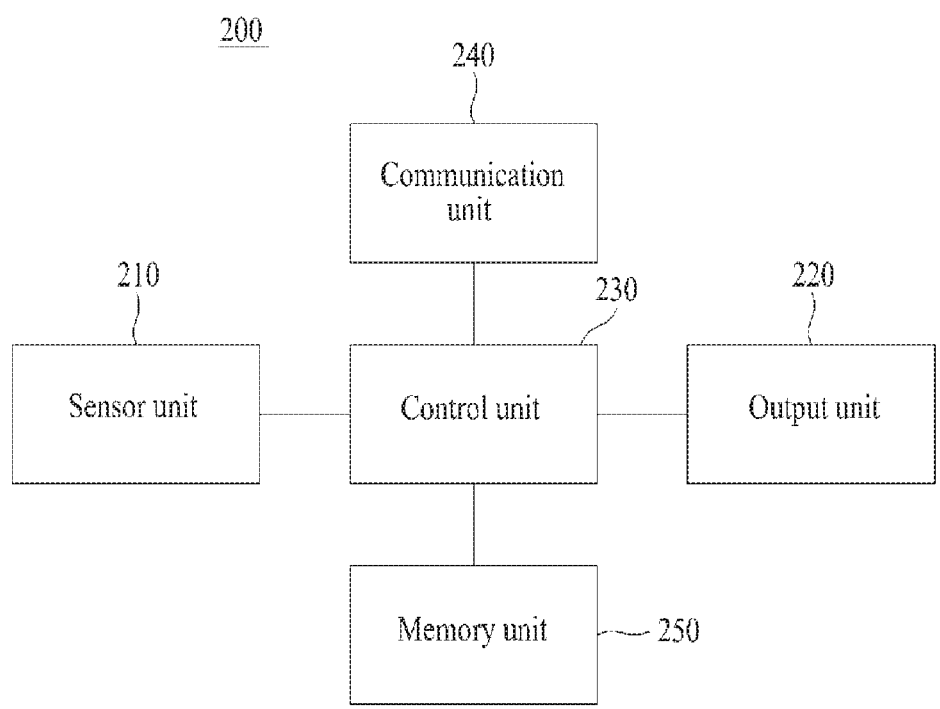
FIG. 4 is a block diagram illustrating a sleep inducing device, according to another embodiment of the present invention.

FIG. 4 is a block diagram illustrating a sleep inducing device, according to another embodiment of the present invention.

Referring to FIG. 4, according to another embodiment of the present invention, a sleep inducing device 200 may include a sensor unit 210, an output unit 220, a control unit 230, a communication unit 240, and a memory unit 250.

The sensor unit 210 may measure bio-information including the brain waves, the heart rate, the respiration, the blood oxygen saturation, the body movements, eyeball movements, the muscle movements, the snoring, the change in body temperature, and the like, and environment information including the illuminance, the humidity, the temperature of a surrounding environment, or the like.

In detail, the sensor unit 210 may include at least one of an electroencephalogram (EEG) sensor, which is to acquire a brain wave of a user, a PPG sensor, which is to acquire oxygen saturation in the blood of the user, an EDA sensor, which is to acquire user's tension, a temperature sensor, which is to acquire the temperature of a user's body, an ECG sensor, which is to acquire a heart rate of the user, an EMG sensor, which is to acquire the movement of user's body muscles, an EOG sensor, which is to acquire the movement of a user's eyeball, a camera, which is to acquire an image of the user, a microphone, which is to acquire the sound generated from the user during the sleeping of the user, a motion sensor, which is to acquire the movement of the user, and an illuminance sensor which is to acquires information on the quantity of light under the surrounding environment of the user.

The output unit 220 may stimulate at least one of user's five senses through at least one of vibration, sound, light, taste, and smell. The output unit 220 may include a first output unit 161 of FIG. 2 and a second output unit 162 of FIG. 2. The first output unit 161 of FIG. 2 may be positioned at one side of housing parts 110 and 150 and may output sound or light of a first frequency. The second output unit 162 of FIG. 2 may be positioned at an opposite side of the housing parts 110 and 150 and may output sound or light of a second frequency different from the first frequency. Accordingly, the output unit 220 may simultaneously output sounds having mutually different frequencies to generate binaural beats. In addition, the output unit 220 may simultaneously output a first light source L1 of FIG. 2 and a second light source L2 of FIG. 2 based on mutually different frequencies. However, the present invention is not limited thereto.

The control unit 230 may control the sensor unit 210 and the output unit 220. The control unit 230 may adjust an output signal of the output unit 220 based on bio-information and environment information measured by the sensor unit 210. In other words, the control unit 230 may adjust an output signal of the output unit 220 through a feedback based on data measured by the sensor unit 210 and may induce the sleep of the user such that the user has the optimal sleep pattern.

In detail, the control unit 230 may calculate the sleep pattern of a user based on a bio-signal (for example, a brain wave signal) measured by the sensor unit 210 and may change the output signal from the output unit 220 such that the sleep pattern approaches a specific value. The control unit 230 may calculate the optimal sleep pattern of the user based on the bio-information and the environment information of the user. Therefore, the control unit 230 adjusts the output frequency of the output unit 220 such that the ratio of the non-REM sleep state to the REM sleep state is in a specific range, thereby adjusting the sleep state of the user. The details thereof will be described below.

In addition, the control unit 230 may measure a response speed of the sleep state of a user according to the change in the output frequency of the output unit 220 and may adjust the change rate in the output frequency based on the response speed. This represents the adaptation of the user for sleep induction. The control unit 230 may adjust entry time into REM sleep or non-REM sleep and holding time in the REM sleep or the non-REM sleep based on the adaptation of the user for the sleep induction. For example, if the adaptation for the induction sleep represents a lower value, the change rate of the output frequency may be increased. If the adaptation for the sleep induction represents a higher value, the change rate of the output frequency may be decreased.

The communication unit 240 may include a wired Interface module, a wireless Internet module, and a short range communication module to make wired/wireless communication with an external device.

The wired Internet module, which refers to a module for wireless Internet access, may make data communication through a wireless communication technology, such as Wireless LAN (WLAN; Wi-Fi), Wireless broadband (Wibro), World Interoperability for Microwave Access (Wimax), High Speed Downlink Packet Access (HSDPA), or the like.

The short range communication module refers to a module for short range communication. A short range communication technology may include Bluetooth, Radio Frequency identification (RFID), Infrared Data Association (IrDa), Ultra Wideband (UWB), ZigBee, or the like.

The wireless interface module receives data or power from an external device to transmit the data or the power to each internal component of the sleep inducing device 200 or to transmit internal data of the sleep inducing device 200 to the external device. For example, a wired/wireless headset port, an external charger port, a wired/wireless data port, a memory card port, an audio I/O. (Input/Output) port, a video I/O (Input/Output) port, an earphone port, a telephone line port, a universal serial bus (USB) port, a LAN line port, a coaxial cable port, or the like may be included in the wired Interface module.

The memory unit 250 may store data measured by the sensor unit 210 in real time, in detail, the memory unit 250 may store sleep information including bio-information and environment information of a user, which are collected through the sensor unit 210. The memory unit 250 may store the information on the optimal sleep pattern. The memory unit 250 may include software, such as a driver, an operating system (OS), an application, or the like necessary for the driving of another component in addition to the control unit 230. The memory unit 250 may include a storage medium corresponding to at least one type of a flash memory, a hard disk, a multimedia card micro type, a card-type memory (for example, an SD or an XD memory), Random Access Memory (RAM), Static Random Access Memory (SRAM), Read-Only Memory (ROM), Electrically Erasable Programmable Read-Only Memory (EEPROM), Programmable Read-Only Memory (PROM), a magnetic memory, a magnetic disk, and an optical disk. In addition, according to the present invention, the sleep inducing device 200 may operate in association with a web storage to perform the storage function of the memory unit 250 over the Internet.

Regarding hardware implementation, the embodiments described therein may be implemented by using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and an electrical unit to perform other functions. Regarding software implementation, embodiments such as procedures and functions described herein may be implemented by using individual software modules. Each software module may perform at least one of functions and operations described herein. Software codes may be implemented by a software application made in a proper program language. Software codes may be stored in the memory unit 250 and may be executed by the control unit 230.

In addition, although not illustrated in drawings, a user input unit may be further included to receive a command from a user. The user input unit may include at least one key button corresponding to at least one command. The key button may be implemented with a hardware key button or a virtual key button on a touch screen. A command, which may be input through the user input unit, may include a command for verifying/outputting information acquired through the sensor unit, a command for selecting a desirable sleep pattern, and a command for controlling an external device.

Figure 5:
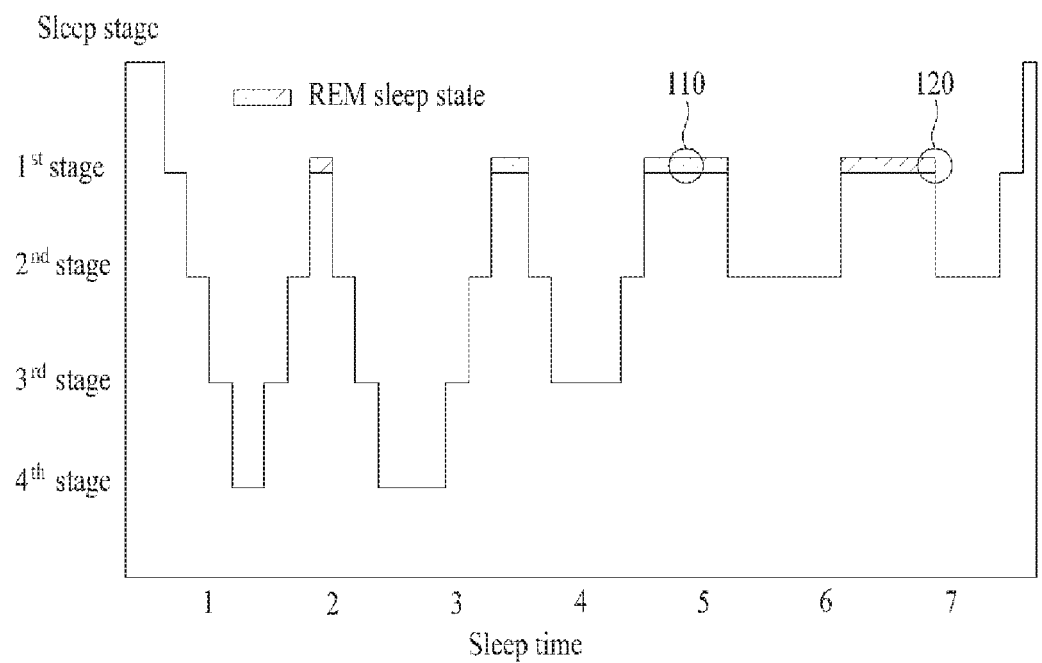
FIG. 5 is a graph illustrating one example of a typical sleep stage.

FIG. 5 is a graph illustrating one example of a typical sleep stage.

Referring to FIG. 5, the typical sleep stage may be divided into first to fourth stages according to generated brain waves. In an initial sleep stage (for example, within 3 hours after sleeping is started), deep non-REM sleep and shallow non-REM sleep alternate stepwise. As a sleep period of time is increased, the ratio of the REM sleep may be increased. In general, if a human being wakes up in a middle stage 110 of a REM sleep state, the human being may not completely wake up and may feel uncomfortable. However, if the human being wakes up at the end of the REM sleep, the human being may completely wake up while feeling less uncomfortable or feeling refreshed.

In addition, each sleep stage has an intrinsic necessary function. If a specific sleep stage period is insufficient or excessive, mental or physical problems (cardiovascular diseases, diabetes, dementia, or the like) may be caused. Accordingly, sleep stages may be proportionally induced such that the function of each stage of sleep is sufficiently exhibited based on a sleep cycle of a person, and a user is prevented from waking up during the sleeping, thereby improving the quality of the sleep. For example, on the assumption that the ratio of deep sleep to REM to shallow sleep is 1:2:1 (25%:50%:25%) is the most ideal ratio, the sleep inducing device of the present invention may induce the sleep stage of the user such that the ratio is maintained during the sleep of the user.

The brain wave is varied with the sleep stages, and even the human body may be varied with the sleep stages. The sleep stage may be calculated using bio-information (for example, a brain wave, a heart rate, respiration, blood oxygen saturation, tossing and turning, snoring, eye movements, muscle movements, body temperature, or the like) and environment information (for example, noise, light, temperature, humidity, or the like) of an examinee. The bio-information and the environment information of the examinee are measured, thereby finding out a sleep pattern representing the change of the sleep stage during the sleeping of the examinee.

In addition, external stimulus is applied through a sense organ of the examinee, thereby inducing the change of the steep stage. For example, if sound or light of a specific frequency is transmitted to a brain through a sense organ, the sleep state may be changed to that of a sleep stage corresponding to the specific frequency (brain wave synchronization theory).

According to the present invention, the sleep inducing device 200 may measure the sleep state of a user, may adjust an output frequency according to the sleep state of the ser, and thus may induce the sleep state to represent the substantially optimal sleep pattern. For example, when the user has difficulty in getting to sleep, the sleep induction may be performed such that the user rapidly gets to sleep, or a desirable form of a sleep brain wave may be continuously induced such that the user is prevented from waking up during the sleeping. In addition, the ratio of non-REM sleep and REM sleep may be adjusted. Accordingly, the sleep inducing device 200 of the present invention may induce the user to have deep sleep and to wake up while feeling refreshed.

Figure 6:
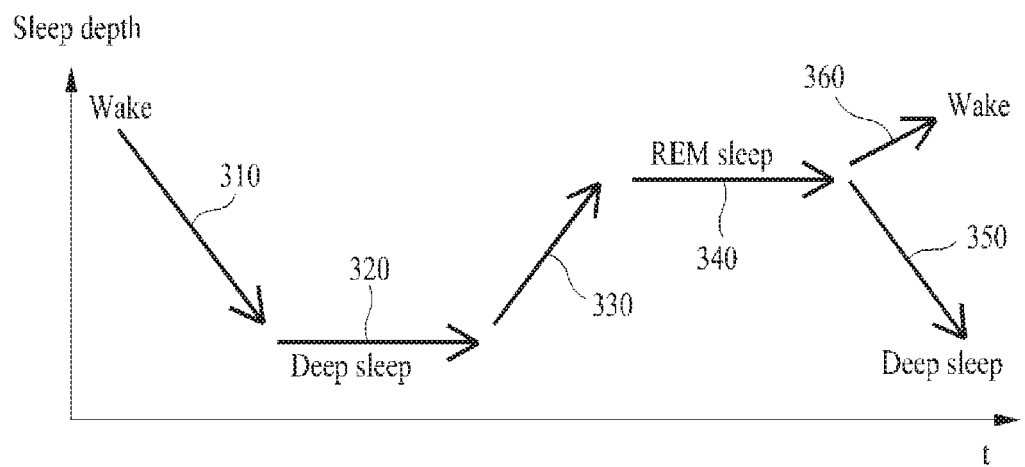
FIG. 6 is a graph illustrating a method of maintaining and changing a sleep state of a user in a sleep inducing device, according to some embodiments of the present invention.

FIG. 6 is a graph illustrating a method of maintaining and changing a sleep state of a user in a sleep inducing device, according to some embodiments of the present invention.

Referring to FIG. 6, according to some embodiments of the present invention, the sleep inducing device may acquire the body information and surrounding environment of a user sensed through a sensor unit, thereby determining the sleep state of the user. In the graph of FIG. 6, a horizontal axis corresponds to time and a vertical axis corresponds to the depth of sleep.

First, the reduction of a sleep stage may be induced such that a user may enter into an initial sleep state from a wake-up state (operation 310). In this case, the control unit 230 may adjust the output signal of the output unit 220 according to a brain wave synchronization response speed. For example, a brain wave signal applied to the user may be reduced in order of 25 Hz→12 Hz→5 Hz→2 Hz to 0.5 Hz. However, the present invention is not limited thereto.

Thereafter, to allow a user to stay in a deep sleep stage at a specific ratio after the user arrives at the deep sleep stage, stimulation having a relevant frequency band (for example, delta wave) is continuously maintained (operation 320). Data on the ideal change of a sleep pattern and the change between sleep stages may be stored in the memory unit 250 in advance. The control unit 230 may adjust the ratio between shallow sleep (or REM sleep) to deep sleep (or non-REM sleep) based on the data stored in the memory 250.

If the sleep stage is naturally changed to the shallow sleep stage (or REM sleep) without continuously being induced by the output signal through the brain wave synchronization, after the induction of stimulation is attempted for a preset time or by the specific number of times which is set in advance, the stimulation may be temporarily stopped. Subsequently, if entrance into the shallow sleep (or REM sleep) is required, the output signal may be randomly applied to the user to make entrance into the shallow sleep stage (operation 330).

Thereafter, if the arrival at the shallow sleep stage (or REM sleep) is detected (operation 340), stimulation is again applied such that a less deep sleep stage is induced based on a personal sleep cycle (operation 350).

In other words, when the change from the sleep state in the deep sleep stage to the sleep state in the shallow sleep stage occurs, an additional attempt is performed based on a preset rule. If an effect is not produced any more, the stimulation is temporarily stopped such that the sleep stage is naturally changed. Thereafter, if the sleep state arrives at a time point in which the sleep state is not lowered to a shallower sleep stage any more (for example, REM sleep appears), stimulation is applied with a frequency band to maintain the REM sleep for a preset time (operation 340) or may be applied for the re-entrance into the deep sleep stage (operation 350).

If a user must be awaken after these procedures are repeated during the sleeping, the user may be awakened by adjusting the frequency count, the intensity, the color change, or the temperature to stimulate a sense organ of the user (operation 360). Accordingly, the sleep inducing device may provide the optimal wake-up state to the user. However, the present invention is not limited thereto. The above-described sleep state change is provided for the illustrative purpose, and may be variously set according to situations.

Figure 7:
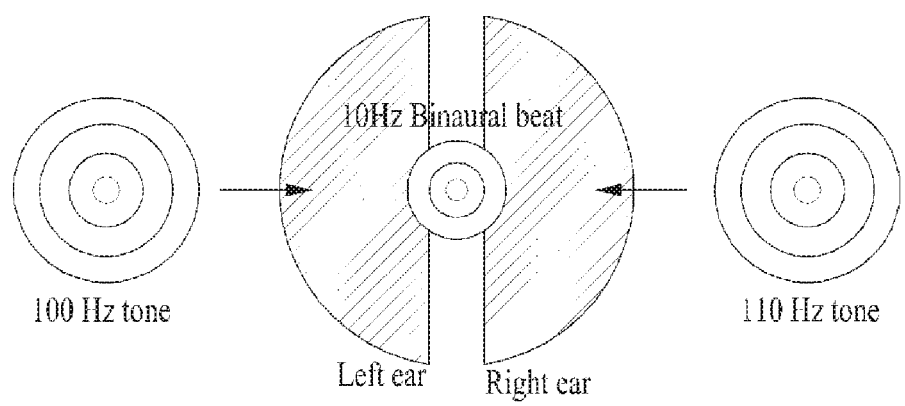
FIG. 7 is a view illustrating an inducing technique based on a brain wave synchronization of a sleep inducing device, according to an embodiment of the inventive concept.

FIG. 7 is a view illustrating an inducing technique based on brainwave synchronization of a sleep inducing device, according to an embodiment of the inventive concept Referring to FIG. 7, to maintain or change the sleep state of a user, the control unit 230 may control the output unit 220 to generate an output signal which reflects a feedback based on a present sleep state and a desirable sleep state of the user.

In detail, the sleep state of a user may be influenced by a wavelength transmitted to the brain of the user to be changed. In this case, to transmit the frequency of a wavelength, which corresponds to the desirable sleep state, to the brain, the control unit 230 may transmit an output signal having a relevant frequency in a binaural beat manner to the brain through the output unit 220. In this case, the binaural beat manner employs a principle of transmitting a wavelength corresponding to the frequency difference between sound waves propagated to a left ear and a right ear to the brain. Therefore, sounds having mutually different frequencies are transmitted to both ears, thereby transmitting a signal having a wavelength desired by the user to the brain. For example, a sound having a first frequency (for example, 100 Hz) is output to one ear through the left first speaker SP1, and a sound having a second frequency (for example, 110 Hz) is output to an opposite ear through the second speaker SP2, thereby transmitting a signal having the wavelength of 10 Hz to the brain. The light source may be applied to achieve the brain wave synchronization by utilizing a specific wavelength, intensity of light, color change of light or color temperature of light. However, the present invention is not limited thereto FIG. 8 is a view illustrating the operation of a sleep inducing device, according to some embodiments of the present invention.

Figure 8:
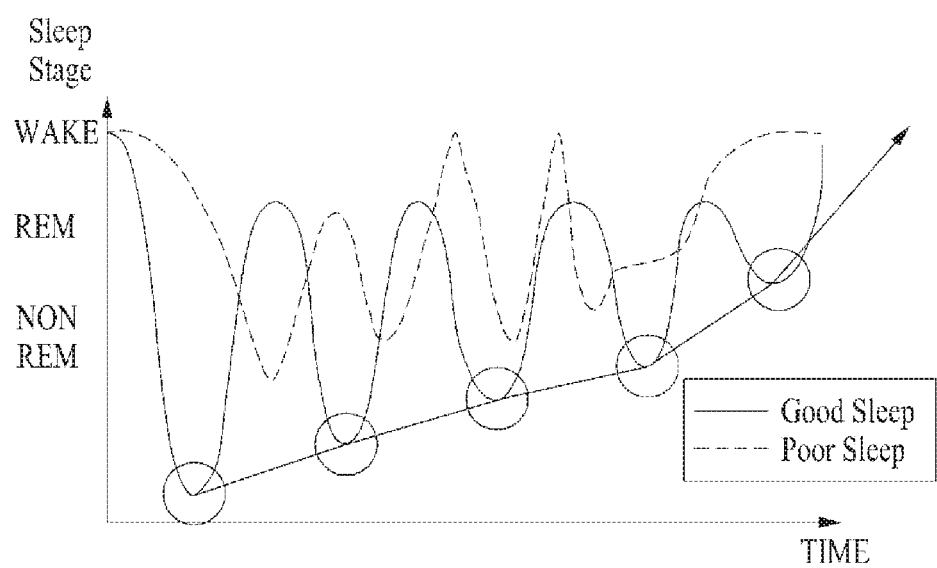
FIG. 8 is a view illustrating the operation of a sleep inducing device, according to some embodiments of the present invention.

Referring to FIG. 8, FIG. 8 illustrates the sleep cycle of a user. On the graph, a first sleep pattern having a good sleep cycle is expressed in a bold line, and a second sleep pattern having a bad sleep cycle is expressed in a dotted line.

In the case of the second sleep pattern, long time is taken until a user arrives at an initial sleep state, and the user does not arrive at a deep sleep state. Accordingly, the user mainly stays only in the shallow sleep state. In addition, the user frequently wakes up during the sleeping. If the user falls asleep in the second sleep pattern, the user wakes up in a fatigued state.

Meanwhile, in the case of the first sleep pattern, a cycle between the shallow sleep stage and the deep sleep stage is constant, shorter time is taken until the user arrives at the deep sleep state, and the ratio between the deep sleep state and the shallow sleep state is constantly maintained.

According to the present invention, the sleep inducing device 200 continuously applies an output signal having a specific wavelength to a user and detects the change of the sleep state of the user based on the output signal, thereby adjusting the output signal such that the user takes sleep substantially having the first sleep pattern.

To accomplish more effective brain wave synchronization, the response speed (that is, brain wave synchronization response speed) of the sleep state of a user may be measured, and the change rate of the output signal may be adjusted based on the response speed. For example, a larger width of stimulation change is applied to the user having a slower response speed in the sleep state, thereby inducing the user to arrive at a desirable sleep state within a shorter time.

In addition, to improve the sleep quality, the reaction change to external stimulation may be exactly analyzed for each user, and the sleep stage may be adjusted based on the reaction variation. In detail, to reduce a fall asleep time (time taken till a user falls asleep after going to bed) and to put the user to a deep sleep, the state change of a sleep stage of each person is analyzed according to external stimulation (for example, temperature change made by adjusting an air conditioner among surrounding devices). Thereafter, based on the reaction degree of a user with respect to the external stimulation, the sleep stage is optimized and induced from a lower stage (an alertness state or a shallow sleep stage, the increase in beta/alpha waves) to a deeper stage (deep sleep, the increase in a delta wave). In other words, the most effective brain wave synchronization phenomenon may be acquired and the sleep state may be actually improved by not only simply analyzing a brain wave, but also analyzing the mutually-complex correlation between various bio-signals.

For example, on the assumption that the sound wave is controlled, and a present brain wave is induced to a low frequency stage from 17 Hz to 2 Hz, instead of inducing the sound wave from a higher frequency to a lower frequency while constantly and continuously reducing the difference between the higher and lower frequencies by 1 Hz, time to reach an value approximate to 16 Hz (+ and − a specific value, such as 0.3 Hz) is measured when the change of 1 Hz is applied, Thereafter, when the sound wave is induced to a lower frequency stage, a change width is changed to adjust the degree of stimulation according to times to reach target approximate values which are set based on different change widths. In other words, stimulation, the change width of which is widened or narrowed, is applied according to the brain wave response speed, thereby substantially optimally adjusting the whole fall asleep time of an individual to match with the brain wave response speed while minimizing the whole fall asleep time, such that the user arrives at a deep sleep state (low frequency region) from an alertness state (high frequency region).

An output signal to stimulate a user may employ not only, a sound wave, which is widened or narrowed, but totally different types of control patterns such as light, temperature, fragrance, moisture, or a touch, which is strong or weak in intensity, color change, a temperature change, or the extent of pressure. The manner of adjusting a stimulation degree for each individual based on the brain wave response speed is applicable to a stimulating manner of maintaining a user in a sleep state after a user falls asleep or awakening the user while the user feels refreshed, as well as a fall asleep time.

In addition, after the optimal timing of awakening a user from the sleeping while feeling refreshed is determined by complexly analyzing a biological signal and surrounding environment information, the user may be awakened in various manners of alarming. Light is preferably exposed in a required time zone for a healthy periodical activity (Melatonin production, or the like) of a physical body during daytime or nighttime. Even when a person is awakened in the morning, light is strongly exposed through a device or a peripheral device (a lamp, an indoor lamp, a stand lamp, or the like), thereby allowing the person to healthily and effectively wake up. In this case, the light is not uniformly exposed with a single constant intensity, but may be provided with color (yellow, blue, or the like), brightness, or flickering of light (frequency) suited to a person while a product continuously learns a bio-signal reaction to stimulation. In other words, the light maybe provided in a manner determined as comfortably awakening the user while allowing the user to feel refreshed. In addition, other stimulation sources (sound, smell, touch, temperature, or the like) may learn specific-pattern stimuli, which allow users to the most comfortably wake up, according to each individual of users and may be provided in various forms. For example, in the case of sound, sound, with which a user feels the most comfortable, may be provided through a time plane while the change in a sleep stage is observed by gradually increasing a volume from a lower state to a higher state, such that the user softly wakes up in over a shallow sleep stage. For example, when the user is switched from a sleep state to a wake-up state, external stimulation may be adjusted stepwise such that the shift to the optimal sleep period is possible. However, the present invention is not limited thereto FIG. 9 is a view illustrating a sleep management system including a sleep inducing device, according to some embodiments of the present invention. For the convenience of explanation, the following description will be made while focusing on the difference from the above description of the previous embodiment without overlapping with the above description.

Referring to FIG. 9, according to an embodiment of the present invention, a sleep management system 1000 may include a sleep inducing device 100, a mobile device 400, and a server 500.

The sleep management device 100 may include the substantially same components as those of the sleep management devices 100 and 200 described with reference to FIGS. 1 to 8 and may operate in the same manner.

The mobile device 400 may be a mobile communication device, such as a PCS having a communication port or a cell phone or may include various types of information terminals, such as a laptop computer, a PC, a personal digital assistant (PDA), a handheld PC (HPC), a web pad, a tablet PC, or the like. The mobile device 400 allows the access to the Internet or a network using a communication port. However, the present invention is not limited thereto. Those skilled in the art may easily reproduce the present invention through different types of mobile communication devices and information terminals based on only the description of the present invention.

Although not clearly illustrated in drawings, the mobile device 400 may include an interface unit, a computing unit, or a display unit. The interface unit may receive bio-information and environment information measured by sensor units S1 to S3 of the sleep inducing device 100. The computing unit may compute sleep pattern information and recommended life pattern information of a user based on the received bio-information and environment information. The display unit displays a sleep pattern and a recommended life pattern on a screen to provide the sleep pattern and the recommended life pattern for the user.

The mobile device 400 may receive the input of the life pattern information based on a question and an answer from the user. The life pattern information may include an age, a gender, an average sleep time, an alcohol intake, a caffeine intake of a user, or the like. The mobile device 400 may transmit the input of the life pattern information, which is received, to the sleep inducing device 100, Thereafter, a control unit 230 of the sleep inducing device 100 calculates a sleep pattern suited to the user, based on the bio-information, the environment information, and the life pattern information of the user, and may change an output signal applied to the user.

The computing unit may create the sleep pattern information based on data measured during the sleeping of the user. The sleep pattern information may include the information on the change of the sleep stage of the user as a function of time. In addition, the computing unit may compute recommended life pattern information including recommended sleep time, recommended wake-up time, a recommended nutrient intake, recommended temperature, or recommended illuminance. The sleep pattern information and the recommended life information calculated by the computing unit may be provided to the user through the display unit.

In addition, the input of the life pattern information received from the user, and the sleep pattern information and the recommended life information of the user are bound into one cluster to be transmitted to the server 500 or the mobile device 400 or to be stored in the device 400 or the server 500.

The server 500 refers to a computer or software to provide service to another computer or a mobile device over a computer network. The server 500 may exchange data with the sleep inducing device 100 or the mobile device 400 by using an information telecommunication network 350. The server 500 may include a preset web-server, a medical institution server, and a social network server (SNS). Accordingly, the server 500 may provide clouding service or web-hard service. The server 500 may provide a platform or a database, which enables a user to store and inquire the life pattern information including personal information, the sleep pattern information, and the recommended life information, to the user.

The information communication network 350 may connect the sleep inducing device 100 with the mobile device 400, may connect the sleep inducing device 100 with the server 500, or may connect the server 500 to the mobile device 400. The information communication network 350 may transmit data using a preset communication protocol. The preset communication protocol may be one of a TCP/IP protocol, a protocol complying with IEEE 802.11, and a WAP protocol. However, the present invention is not limited thereto The mobile device 400 and the sleep inducing device 100 may make communication using a wireless Internet module or a short range communication module without using the information communication network 350. The wireless Internet module, which refers to a module for wireless Internet connection, may make data communication through a wireless communication technology, such as Wireless LAN (WLAN) Wi-Fi, Wireless broadband (Wibro), World Interoperability for Microwave Access (Wimax), High Speed Downlink Packet Access (HSDPA), or the like.

The short range communication module refers to a module for short range communication. The short range communication technology may include Bluetooth, Radio Frequency Identification (MD), infrared Data Association (IrDa), Ultra Wideband (UWB), ZigBee, or the like.

The mobile device 400 may run a sleep management application.

The sleep management application may provide users with a data visualization function, a personal sleep management function, an SNS interworking function, and a time difference adaptation functions.

The data visualization function may provide a user with a material, which is obtained by visualizing the sleep pattern information of the user received from the sleep inducing device 100, using a graph or a table.

The personal sleep management function may provide a user with recommended life pattern information calculated based on the life pattern information input by the user and the sleep pattern information measured by the sleep inducing device 100 and customized to the user. For example, the recommended life pattern information including recommended sleep time, recommended wake-up time, a recommended nutrient intake (for example, a caffeine intake or an alcohol intake), recommended temperature in a sleeping space, or recommended illuminance in the sleeping space. In addition, the optimal nap time, which is applicable to a daily life, may be suggested to a user.

The SNS interworking function may provide a user with a service allowing sharing the sleep pattern information of the user and the information of surrounding areas, ages, genders, or acquaintances that undergo similar experiences or are improved in sleep through an SNS.

The time difference adaptation function may provide a user with a solution to time difference adaptation which occurs in the movement between nations.

In detail, the sleep inducing device 100 calculates the sleep adaptation of a user based on the change speed of the bio-information of the user according to the change of an output signal. The sleep adaptation is transmitted to the mobile device 400.

Thereafter, the mobile device 400 receives travel time difference information from the user. The travel time difference information may include information on a departure country, a destination country, time difference adaptation days of a user, or the like.

Thereafter, recommended sleep information including recommended sleep time and recommended wake-up time may be calculated based on the sleep adaptation received from the sleep inducing device 100 and the travel time difference information received from the user and may be displayed on a display unit.

For example, when the time difference is made between the travel departure location and the travel destination location, the mobile device 400 may calculate the time difference adaptation days based on the sleep cycle, the age, and the gender of the user or may receive the input of the time difference adaptation days from a user. The mobile device 400 may provide a user with recommended sleep time or recommended wake-up time based on the time difference adaptation days. However, the present invention is not limited thereto.

In addition, the time difference adaptation function may be stored in a memory unit 250 of the sleep inducing device 100 and used.

FIG. 10 is a view illustrating the operation of a sleep management system including a sleep inducing device, according to some embodiments of the present invention. For the convenience of explanation, the following description will be made while focusing on the difference from the above description of the previous embodiment without overlapping with the above description.

Referring to FIG. 10, the sleep management system 1100 may communicate with a plurality of devices through various wireless communication schemes. Although not clearly illustrated in drawings, to implement a network system based on an Internet of things (IoT) object, each of the devices 2200 to 2600, including a lighting device 2100 may include at least one communication module. According to an embodiment, the lighting device 2100 may be communicatively connected with the sleep management system 1100 by a wireless communication protocol, such as WiFi, Zigbee, or LiFi. To this end, the lighting device 2100 may have at least on lamp control module 2110.

The devices 2100 to 2600 communicatively connected with the sleep management system 1100 based on the IoT include a lighting device 2100, a television 2200, a central control device 2300, an air conditioner 2400, a heater 2500, a dehumidifier 2600, and the like.

The central control device 2300 may wirelessly control an automatic-curtain adjusting unit 2310, a digital door lock 5400, or an automatic-window opening/closing device 2330.

The sleep management system 1100 may control operations of the devices 2100 to 2600 based on the sleep state of a user through a wireless communication network (Zigbee, WiFi, LiFi, or the like) installed at home. For example, the sleep management system 1100 may automatically adjust the illuminance of the lighting device 2100 according to the sleep state of the user. In addition, the sleep management system 1100 may adjust the internal illuminance of a room and the ventilation state of the room by turning on/off a television 2200 or by using the central control device 2300 based on the sleep state or the bio-information of the user. The interior temperature may be adjusted by controlling the air-conditioner 2400 or the heater 2500 or the interior humidity may be adjusted by controlling the dehumidifier 2600.

Meanwhile, the sleep management system 1100 may be utilized as a device which maintains building security or detects and copes with an emergency situation. For example, if a smoke or temperature sensor is attached to the lighting device 2100, the fire may be rapidly detected and notified to a user, thereby minimizing damages. In addition, the central control device 2300 may be controlled based on an outside weather or an amount of sunshine, thereby saving energy and providing fresh lighting environment.

Additionally, the sleep management system 1100 may collect and analyze a pattern of data on the sleep quality of a user and may provide the user with a service to suggest time to go to bed, sleep time, wake-up time, and a nap time such that the quality of the optimized sleep is maintained. For example, the sleep management system 100 may maintain the sleep quality of the user at a specific level or more based on snoring, frequent tossing and turning, the change of a shallow sleep, or the like. The sleep management system 1100 interworks with schedules of an electronic device (a smart phone, a PDA, a tablet PC, or the like) to receive a daytime or an early sleep time, at which schedules are not made, from the server 500. Alternatively, a device itself may provide a behavior manual for the user in the middle of a daily schedule in an alarming manner to improve the quality of the sleep, which has been insufficient during the last nighttime.

In addition, the sleep management system 1100 may provide a user with information such as detailed sleep time, wake-up time, a nutrient intake (for example, a caffeine intake or an alcohol intake), recommended temperature or recommended illuminance through feedback by the mobile device 400 (for example, a smart phone, a PDA, a tablet, or a computer). The feedback information may help a user improve the quality of the sleep of the user.

The sleep management system 1100 may share information with another bio-signal information collecting device. For example, the sleep management system 1100 may receive share data, which is measured by a device (a bangle type, a bracelet type, an attachment type, or the like) to measure a workout amount, a calorie intake, a heart rate, a respiration information, stress information, or information on an amount of conversation during the daytime or the nighttime of the user. The sleep management system 1100 may utilize received data in the change of a sleep stage of the user and the improvement in induction of the optimized sleep of the user. In other words, according to the present invention, the sleep management system 1100 may manage and improve the whole life style of a user as well as the sleep time of the user. For example, the sleep management system 1100 may analyze the quantitative relation between the workout amount or the caffeine intake of the user and the sleep quality of the user and may suggest recommended workout amount and recommended caffeine intake which is suited to the user.

The sleep management system 1100 may transmit the bio-information or the life pattern information of a user to the server 500 in a medical institution and may provide the feedback on the information to the user through the mobile device 400. The sleep management system 1100 may analyze measured data and may recommend a hospital visit when serious signs are found to require hospital treatment. When an emergency situation (for example, sleep apnea, or the like) occurs to a user during the sleeping of the user, the sleep management system 1100 may provide an automatic notification service to contact the nearest emergency center or a pre-registered contact network.

Although the embodiments of the present invention have been described with reference to accompanying drawings, it is understood that the present invention should not be limited to these embodiments but various changes and modifications can be made by one ordinary skilled in the art within the spirit and scope of the present invention as hereinafter claimed.

The invention claimed is:

1. A sleep inducing device comprising:
   a housing unit including a frame allowing shape transformation;
   a sensor unit provided on a first surface of the housing unit and including a brain-wave measurement sensor measuring a brain wave signal of a user;
   an output unit including a first output unit that is positioned at a first side of the housing unit and outputs sound or light of a first frequency, and a second output unit that is positioned at a second side of the housing unit opposite from the first side and outputs sound or light of a second frequency different from the first frequency; and
   a control unit that calculates a sleep pattern of the user based on the brain-wave measurement measured by the sensor unit and changes an output signal of the output unit such that the sleep pattern approximates a specific value,
   wherein the output unit includes:
      a speaker unit including a first speaker that outputs the first frequency and a second speaker that outputs the second frequency making a difference from the first frequency by a first wavelength; and
      a light source part including a first light source that adjusts an intensity of light based on a change of the first frequency and a second light source that adjusts an intensity of the light based on a change of the second frequency.

2. The sleep inducing device of claim 1, wherein the housing unit includes:
   a cover part including the frame, which is formed in an eye patch shape and allows the shape transformation suitable for a head of the user; and
   an elastic part making contact with a first surface of the cover part and including a material having elasticity.

3. The sleep inducing device of claim 1, wherein, in the housing unit, an angle between a central portion and a side end portion is adjusted from a first angle to a second angle by external force.

4. The sleep inducing device of claim 1, wherein the sensor unit further includes:
   a temperature sensor provided on the first surface of the housing unit and positioned on a same plane as the brain-wave measurement sensor; and
   an illuminance sensor or a humidity sensor provided on a second surface of the housing unit opposite from the first surface.

5. The sleep inducing device of claim 1, further comprising:
   a memory unit that stores data measured by the sensor unit in real time; and
   a communication unit that wirelessly transmits the stored data to an external device.

6. The sleep inducing device of claim 5, wherein the data includes information on a brain wave or a body temperature of the user, or illuminance or humidity of an outside.

7. The sleep inducing device of claim 1, wherein the control unit adjusts a sleep state of the user by adjusting an output frequency of the output unit such that a ratio between a REM sleep state and a non-REM sleep of the user is in a preset range.

8. The sleep inducing device of claim 6, wherein the control unit measures a response speed of a sleep state of the user based on a change in an output frequency of the output unit and adjusts a change rate of the output frequency based on the measured speed.

* * * * *